United States Patent
Goodwin et al.

(10) Patent No.: US 7,179,217 B2
(45) Date of Patent: Feb. 20, 2007

(54) APPARATUS FOR ENHANCING TISSUE REPAIR IN MAMMALS

(75) Inventors: Thomas J. Goodwin, Kemah, TX (US); Clayton R. Parker, Safety Harbor, FL (US)

(73) Assignees: Regenetech, Inc., Sugar Land, TX (US); The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 11/169,614

(22) Filed: Jun. 29, 2005

(65) Prior Publication Data

US 2006/0229487 A1    Oct. 12, 2006

(51) Int. Cl.
*A61N 2/00* (2006.01)
(52) U.S. Cl. ......................................................... 600/9
(58) Field of Classification Search ............... 600/9–15
See application file for complete search history.

(56) References Cited

U.S. PATENT DOCUMENTS

| | | | |
|---|---|---|---|
| 4,993,413 A * | 2/1991 | McLeod et al. ............ | 607/2 |
| 5,030,225 A | 7/1991 | Aebischer et al. | |
| 5,224,922 A * | 7/1993 | Kurtz .......................... | 600/13 |
| 6,485,963 B1 | 11/2002 | Wolf et al. | |
| 2003/0158585 A1* | 8/2003 | Burnett ......................... | 607/2 |

* cited by examiner

Primary Examiner—John P. Lacyk
(74) Attorney, Agent, or Firm—Ladas & Parry LLP

(57) ABSTRACT

An apparatus is disclosed for enhancing tissue repair in mammals, with the apparatus comprising: a sleeve for encircling a portion of a mammalian body part, said sleeve comprising an electrically conductive coil capable of generating an electromagnetic field when an electrical current is applied thereto, means for supporting the sleeve on the mammalian body part; and means for supplying the electrically conductive coil with a square wave time varying electrical current sufficient to create a time varying electromagnetic force of from approximately 0.05 gauss to 0.05 gauss within the interior of the coil in order that when the sleeve is placed on a mammalian body part and the time varying electromagnetic force of from approximately 0.05 gauss to 0.05 gauss is generated on the mammalian body part for an extended period of time, tissue regeneration within the mammalian body part is increased to a rate in excess of the normal tissue regeneration rate that would occur without application of the time varying electromagnetic force.

1 Claim, 2 Drawing Sheets

APPARATUS FOR ENHANCING TISSUE REPAIR IN MAMMALS

ORIGIN OF THE INVENTION

The invention described herein was made in part by an employee of the United States Government and may be manufactured and used by and for the Government of the United States for governmental purposes without the payment of any royalties thereon or therefor.

FIELD OF THE INVENTION

The present invention relates to an apparatus for enhancing tissue repair in mammals. More particularly, the present invention relates to a sleeve that fits over a mammalian body part. The sleeve is in the form of an electromagnetic coil. The sleeve is placed on a mammalian body part, e.g. a human leg or arm or a dog, cat, or horse leg. A square wave (Fourier curve) time varying electromagnetic current is applied to the coil to create a time varying electromagnetic force of from 0.05 gauss to 0.5 gauss within the center of the coil. The time varying electromagnetic force is transmitted to the mammalian body part for a sustained period of time. Preferably, the mammal is provided with a diet or given a supplement that increases the amount of calcium ions ($Ca^+$ or $Ca^{++}$) ions in the mammal during the treatment. The present invention is helpful in enhancing tissue repair in mammals and is particularly useful in accelerating repair of broken bones.

BACKGROUND OF THE INVENTION

The power of the magnet is one of the most basic powers in nature. We know that magnetism itself was an ingredient in the primordial soup from which the universe and our planet came forth. Magnetism is the force that keeps order in the galaxy, allowing stars and planets to spin at significant velocities. And in a sense, our own planet's magnetic field is responsible for protecting all life on earth.

Bio-magnetic therapy has long been the subject of controversy. Actually, bio-magnetic therapy is not new to everyone. Many veterinarians have been aware of bio-magnetic benefits for years, and use magnets to heal fractures quickly, thereby saving the lives of racehorses and other animals. Doctors treating professional athletes commonly recommend magnets to speed up recovery from painful injuries. And other physicians in a variety of specialties, including dermatologists, internists, pediatricians, and surgeons, have used magnets with varying claims of success.

The theory of magnetic healing can be seen by looking at early records of scientifically advanced civilizations, which tell us that magnetic forces have long been prized for their restorative properties. Ancient Greece discovered the very first natural magnet in the form of the lodestone, and Hippocrates, the father of medicine, noted its healing powers. The Egyptians, too, described the divine powers of the magnet in their writings, and Cleopatra frequently adorned herself with magnetic jewelry to preserve youthfulness. Chinese manuscripts dating back thousands of years describe the Eastern belief that the life force, termed "qi", is generated by the earth's magnetic field. Today, many believe that certain places on earth, such as Lourdes, France, and Sedona, Arizona, owe their healing powers to naturally high levels of this qi, or bio-magnetic energy.

Magnetic therapy is used in many countries such as Japan, China, India, Austria, and Germany. Although state-of-the-art American medicine uses techniques to monitor magnetic fields, such as electrocardiograms, electroencephalograms, and magnetic resonance imaging, it has not taken other forms of magnetic therapy seriously. More and more American studies, however, are considering whether or not magnetic therapy has medicinal value. As a result, increasing numbers of people are sleeping on magnetic beds at night and wearing small magnets during the day for greater energy, preventive purposes, and healing, many claiming varying degrees of success.

Research into magnet therapy is divided into two distinct areas: pulsed bioelectric magnetic therapy and fixed magnetic therapy. Probably 85 to 90 percent of the scientific literature is on pulsed bioelectric bio-magnetic therapy; the remainder is on therapy with fixed solid magnets.

There are different schools of thought on the essential mechanisms of magnetic therapy, centered on questions of polarity, among other issues. However, fixed magnetic therapy has yet to be widely accepted by the scientific and medical community.

The effectiveness of using pulsed magnetic fields to heal bone fractures and, to a lesser degree, soft tissue injures such as sprains and strains, has been debated for some time. Numerous scientific journals have reported these findings since the 1970s, and the FDA approves the use of pulsed electromagnetic fields for the treatment of nonunion bone fractures, which are fractures that will not heal on their own. It is believed that the pulsed electromagnetic fields penetrate the cast and get to the layer of skin that's moist and conductive. Then the electric field stops, but the magnetic field continues to do the healing work.

Numerous scientists have advanced theories for electromagnetic healing of many ailments, including osteoarthritis, rheumatoid arthritis, fibromyalgia, tension headaches, migraines, and Parkinson's disease.

All of the prior attempts to use electromagnetic therapy have used high levels of electromagnetism usually 50 gauss or more. While most of this therapy has used flat magnetic generators, a few have wrapped a magnetic blanket around a body member to attempt to regenerate or heal the body part. Some of the attempts have used pulsed waves, but such pulsed waves have been either on-off pulses or sinusoidal waves. No one, prior to this invention, has found the key to electromagnetic regeneration of mammalian tissue.

This invention has finally found the long sought after key to utilization of electromagnetic forces for tissue regeneration. To be successful in tissue regeneration, the electromagnetic force must be a square wave (Fourier curve) time varying electromagnetic wave at a level of from approximately 0.05 gauss to 0.5 gauss, a much lower level than previously contemplated by anyone. Other types of pulsating waves and much higher levels of electromagnetic force do not achieve the success of this invention.

SUMMARY OF THE INVENTION

This invention includes an apparatus for enhancing tissue repair in mammals, said apparatus comprising: a sleeve for encircling a portion of a mammalian body part, said sleeve comprising an electrically conductive coil capable of generating an electromagnetic field when an electrical current is applied thereto, means for supporting the sleeve on the mammalian body part; and a means for supplying the electrically conductive coil with a square wave time varying electrical current sufficient to create a time varying electromagnetic force of from approximately 0.05 gauss to 0.5 gauss within the interior of the coil in order that when the sleeve is placed on a mammalian body part and the time varying electromagnetic force of from approximately 0.05 gauss to 0.5 gauss is generated on the mammalian body part for an extended period of time, tissue regeneration within the mammalian body part is increased to a rate in excess of the normal tissue regeneration rate that would occur without application of the time varying electromagnetic force. The electrically conductive coil is preferably a ferromagnetic material, such as wire, with approximately ten windings per inch. The sleeve can be placed on a body part, e.g. an arm or a leg, of the mammal and the body part exposed to the 0.05 gauss to 0.5 gauss time varying electromagnetic force for an extended period of time to enhance tissue repair, such increasing the healing rate of bone fracture repair or increased healing rate of ulcerated skin. It is preferable that the treated mammal have the mammal has an increased level of calcium ions (Ca+ or Ca++) during the application of the time varying electromagnetic force.

This invention also includes the process of using the described apparatus to enhance tissue repair in mammals.

DETAILED DESCRIPTION OF THE INVENTION

Figure 1:
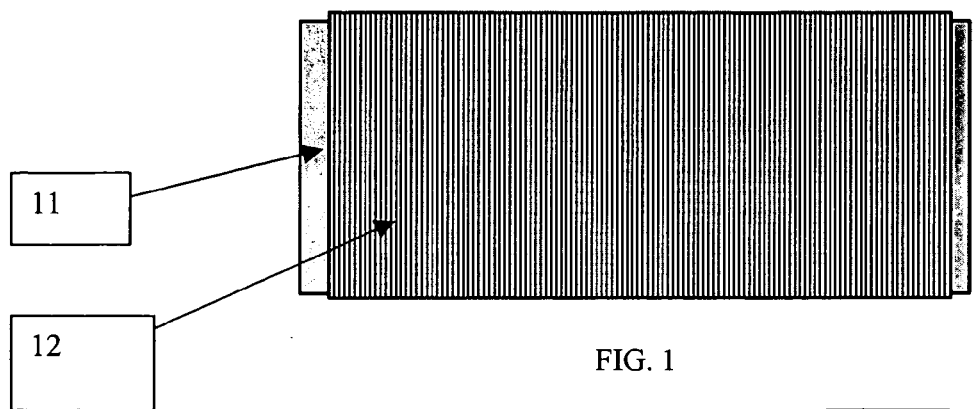
FIG. 1 is a side view of the sleeve of this invention showing the coil wound around the sleeve.
Figure 2:
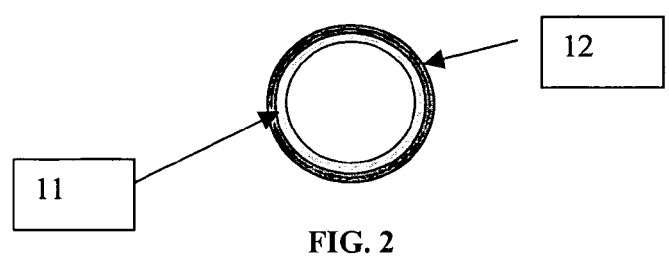
FIG. 2 is an end view of showing the coil on the sleeve.
Figure 3:
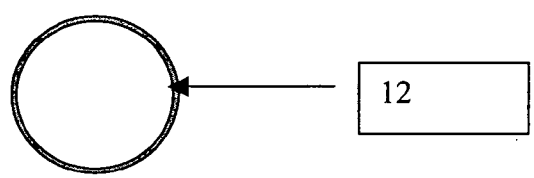
FIG. 3 is an end view of the coil.
Figure 4:
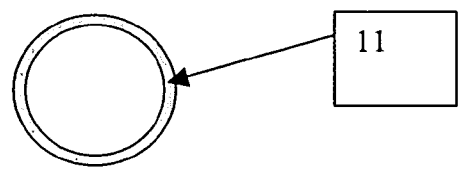
FIG. 4 is an end view of the sleeve.
Figure 5:
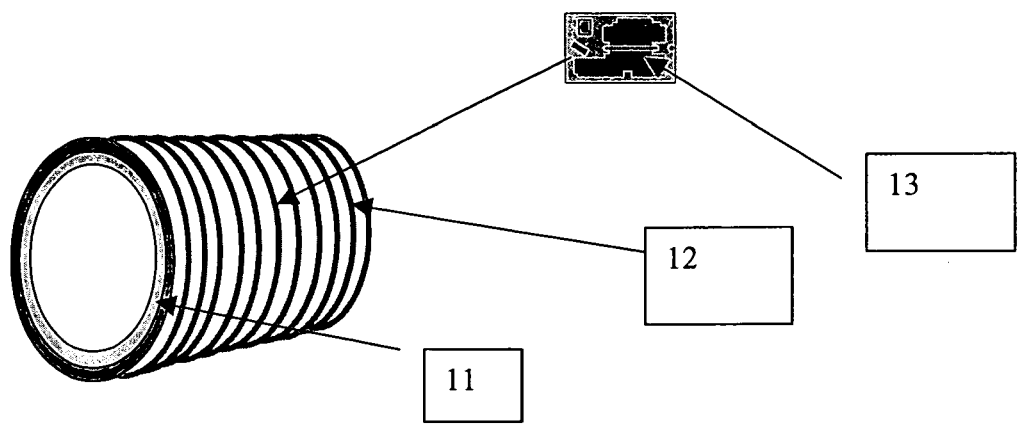
FIG. 5 is a perspective view of the sleeve with the coil and the time varying electrical current generator.
Figure 6:
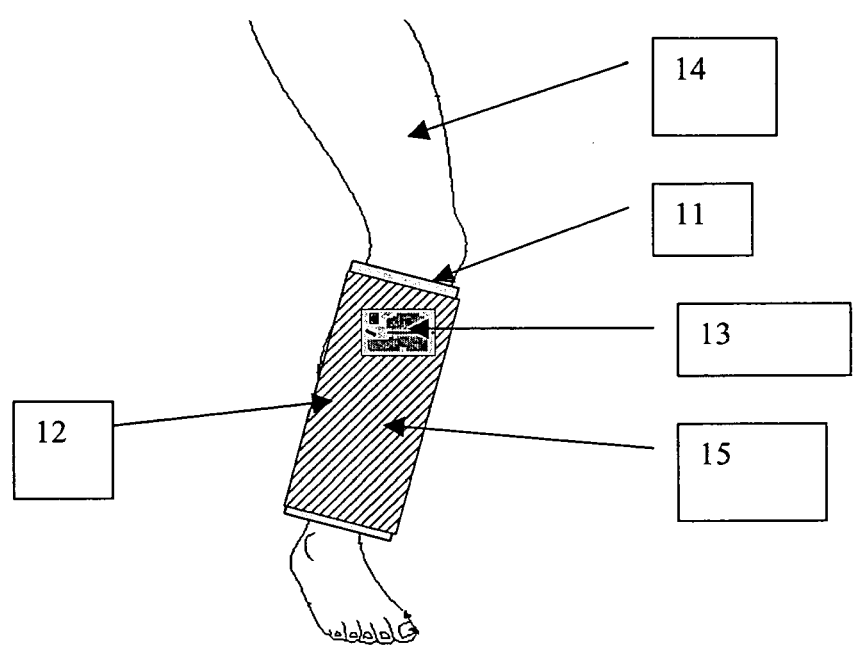
FIG. 6 is an illustration of the sleeve on a human leg.

This invention may be more fully described, but is not limited by the attached drawings and ensuing description in which, referring to the drawings, a sleeve portion 11 has a wire coil 12 wound around it. The sleeve portion is such that it fits over the mammalian body part to be treated. The wire coil is wound around the sleeve at approximately 10 windings per inch. A time varying electrical generator 13 is designed to be attached to the wire coil 12. The time varying electrical generator 13 is a standard part that can be purchased in stores supplying electrical products. It is powered by a standard 9-volt battery (not shown) and can be affixed to the sleeve by means of choice such as glue or Velcro (TM Velcro Industries B.V.). It must be capable of generating a time varying electromagnetic force of 0.05 to 0.5 gauss within the sleeve. The sleeve is then placed on a mammalian body part such as human leg 14 to effect tissue regeneration thereof. The sleeve is kept on the body part for at least a week. Preferably, the mammal being treated is given an over the counter calcium supplement during the treatment.

If two groups of mammals having simple leg fractures are separated and one is given standard treatment and the other group has the time varying electromagnetic force applied to it with the sleeve, those being treated with the time varying electromagnetic force will have substantially reduced healing times.

We claim:

1. A method of increasing tissue repair in a mammalian body part comprising:

providing a mammal with an increased level of calcium ions (Ca+ or Ca++);

maintaining an increased level of calcium ions (Ca+ or Ca++) throughout the method of repair;

encompassing the mammalian body part with an apparatus for enhancing tissue repair, said apparatus comprising a sleeve for encircling a portion of a mammalian body part, said sleeve comprising an electrically conductive coil capable of generating an electromagnetic field when an electrical current is applied thereto, means for supporting the sleeve on the mammalian body part; and means for supplying the electrically conductive coil with a square wave time varying electrical current sufficient to create a time varying electromagnetic force of from approximately 0.05 gauss to 0.5 gauss within the interior of the coil; and generating a time varying electromagnetic force of from approximately 0.05 gauss to 0.5 gauss on the mammalian body part by applying a time varying electrical current to the coil for an extended period of time so that tissue regeneration within the mammalian body part is increased to a rate in excess of the normal tissue regeneration rate that would occur without application of the time varying electromagnetic force.

* * * * *

UNITED STATES PATENT AND TRADEMARK OFFICE
CERTIFICATE OF CORRECTION

PATENT NO.        : 7,179,217 B2
APPLICATION NO.   : 11/169614
DATED             : February 20, 2007
INVENTOR(S)       : Goodwin et al.

It is certified that error appears in the above-identified patent and that said Letters Patent is hereby corrected as shown below:

On the title page item (57), lines 10, 13-14, should read -- 0.05 gauss to 0.5 gauss --.

Signed and Sealed this

Tenth Day of April, 2007

JON W. DUDAS
*Director of the United States Patent and Trademark Office*